United States Patent [19]

Grieder et al.

[11] 4,266,071
[45] May 5, 1981

[54] PROCESS FOR THE PREPARATION OF N-(1-ALKOXYCARBONYLETHYL)-2,6-DIALKYLANILINES

[75] Inventors: Alfred Grieder, Böckten; Klaus-Jürgen Coers, Reinach, both of Switzerland

[73] Assignee: Ciba-Geigy Corporation, Ardsley, N.Y.

[21] Appl. No.: 157,760

[22] Filed: Jun. 9, 1980

[51] Int. Cl.$^3$ .................................... C07C 101/44
[52] U.S. Cl. .................................................. 560/43
[58] Field of Search ......................................... 560/43

[56] References Cited

U.S. PATENT DOCUMENTS

| Re. 29,468 | 11/1977 | Clayton | 560/43 |
| 2,273,556 | 2/1942 | Bean | 560/43 |
| 3,402,195 | 9/1968 | Bolhofer | 560/43 X |
| 3,882,162 | 5/1975 | Clayton | 560/43 |
| 4,008,066 | 2/1977 | Moser | 71/76 |
| 4,025,648 | 5/1977 | Hubele | 560/43 X |
| 4,032,657 | 6/1977 | Moser | 560/43 X |

FOREIGN PATENT DOCUMENTS 572017 1/1976 Switzerland .

Primary Examiner—Paul F. Shaver
Attorney, Agent, or Firm—Karl F. Jorda

[57] ABSTRACT

A process is described for the preparation of N-(1'-alkoxycarbonylethyl)-2,6-dialkylanilines of the formula

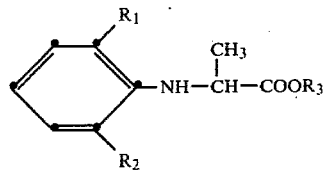

in which $R_1$ and $R_2$ are each methyl or ethyl and $R_3$ is an alkyl group having 1 to 4 carbon atoms, this process being based on the reaction of a corresponding 2,6-dialkylaniline with a corresponding alkyl 2-bromopropionate. The process is carried out by carrying out the reaction of the 2,6-dialkylaniline with the alkyl 2-bromopropionate at 110° to 125° C. in excess 2,6-dialkylaniline as the solvent, in the presence of a quaternary compound of nitrogen or of phosphorus, and in the presence of an alkali metal carbonate or alkali metal bicarbonate as an acid acceptor, distilling off the water formed during the reaction and working up the organic phase, which is obtained after adding water and separating the phases, by distillation.

The N-(1'-alkoxycarbonylethyl)-2,6-dialkylanilines of the above formula which can be prepared by this process are valuable intermediates for the preparation of compounds having a pesticidal action.

14 Claims, No Drawings

PROCESS FOR THE PREPARATION OF N-(1-ALKOXYCARBONYLETHYL)-2,6-DIALKYLANILINES

The present invention relates to a process for the preparation of N-(1'-alkoxycarbonylethyl)-2,6-dialkylanilines of the formula I

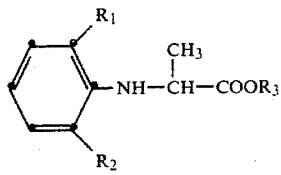

in which $R_1$ and $R_2$ are each methyl or ethyl and $R_3$ is an alkyl group having 1–4 carbon atoms, by reacting a 2,6-dialkylaniline of the formula II

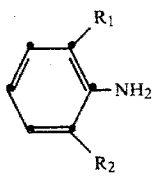

in which $R_1$ and $R_2$ are as defined above, with an alkyl 2-bromopropionate of the formula III

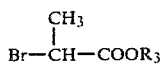

in which $R_3$ is as defined above.

The N-(1'-alkoxycarbonylethyl)-2,6-dialkylanilines of the formula I are valuable intermediates for the preparation of compounds having a pesticidal action. They can, for example, be converted by reaction with acid chlorides, such as chloroacetyl chloride, methoxyacetyl chloride or furan-2-carboxylic acid chloride, into corresponding N-acylanilines, which are distinguished by an outstanding action against phytopathogenic microorganisms and therefore find extensive use in plant protection. N-Acylanilines of this type, and also their preparation and use, are described, for example, in U.S. Pat. Nos. 4,008,066, 4,094,990 and 4,151,299.

Particularly preferred N-acylanilines of the abovementioned type, which can be prepared by acylation of the N-(1'-alkoxycarbonylethyl)-2,6-dimethylanilines of the formula I which can be prepared according to the invention, are N-methoxyacetyl-N-(1'-methoxycarbonylethyl)-2,6-dimethylaniline and N-(2''-furoyl)-N-(1'-methoxycarbonylethyl)-2,6-dimethylaniline.

The preparation of N-(1'-alkoxycarbonylethyl)-2,6-dialkylanilines of the formula I by reacting 2,6-dialkylanilines of the formula II with α-halogenopropionic acid esters of the formula III presents problems, on the one hand because of steric hindrance due to the alkyl groups in the ortho-position and on the other hand because of the sensitivity of the α-halogenopropionic acid esters to hydrolysis. Various proposals have already been made for solving the problems associated with carrying out this process.

It is known to prepare N-alkoxycarbonylmethyl-2,6-dialkylanilines by reacting α-halogenoacetic acid esters and 2,6-dialkylanilines in the presence of aqueous alkali metal hydroxides. Because of side reactions, such as N,N-dialkylation and hydrolysis of the ester group, the desired products are obtained only in inadequate purity and in unsatisfactory yields by this method. (U.S. Pat. No. 3,882,162).

It has already been proposed to avoid the disadvantages of the abovementioned process by carrying out the reaction of the 2,6-dialkylaniline with the α-halogenocarboxylic acid ester in the presence of excess 2,6-dialkylaniline, as an acid-binding agent, and in the presence of a catalytic amount of the hydrochloride of the particular 2,6-dialkylaniline, at temperatures of 100° to 250° C. However, with this process also the yields achievable are below 70% of theory (U.S. Pat. No. 3,882,162).

Furthermore, it has already been proposed to react anilines substituted in the nucleus, at temperatures of 100° to 175° C., in the presence of a tertiary amine as an acid-binding agent, with α-halogenocarboxylic acid esters, and, according to a preferred embodiment of this process, the reaction is carried out in excess ester as the solvent and, in order to accelerate the reaction, the tertiary amine is already added in the form of a salt, for example in the form of the hydrochloride, at the start of the reaction. With this process, aniline conversions of 90 to 96%, a selectivity of 78 to 90% and yields of N-(1'-alkoxycarbonylalkyl)-anilines of 70–86% of theory are obtained; the yields quoted are based not on the pure product actually isolated, but on an analytical determination of the content of pure product in the crude product. (Swiss Pat. No. 572,017).

Furthermore, the reaction of 2,6-dimethylaniline at 120° to 125° C., in the presence of sodium bicarbonate as an acid-binding agent, with a three-fold molar excess of methyl 2-bromopropionate has been disclosed in U.S. Pat. No. 4,008,066. With this process, N-(1'-methoxycarbonylethyl)-2,6-dimethylaniline is obtained in a yield of 79.6% of theory.

As is shown by the above survey of the prior art, it is not possible with the processes disclosed hitherto to prepare N-(1'-alkoxycarbonylethyl)-2,6-dialkylanilines in satisfactory yield and purity. It is, therefore, the object of the present invention to provide a process which avoids the disadvantages of the known processes and which enables N-(1'-alkoxycarbonylethyl)-2,6-dialkylanilines of the formula I to be prepared in satisfactory yield and purity in a simple manner.

According to the present invention, it is proposed that the reaction of the 2,6-dialkylaniline of the formula II with the alkyl 2-bromopropionate of the formula III be carried out in excess 2,6-dialkylaniline as the solvent, at 110° to 125° C., in the presence of a quaternary compound of the formula IV

in which Q is nitrogen or phosphorus, the radicals $R_4$, $R_5$, $R_6$ and $R_7$ are each an alkyl radical having 1 to 16 carbon atoms, or phenyl, and one of the radicals $R_4$, $R_5$, $R_6$ and $R_7$ can also be benzyl, and, if Q is nitrogen, Q together with three of the radicals $R_4$, $R_5$, $R_6$ and $R_7$ can also be a pyridine radical, whilst the fourth radical is alkyl having 1–16 carbon atoms, phenyl or benzyl, and $X^\ominus$ is a halide anion or a bisulfate anion, and in the presence of an alkali metal carbonate or alkali metal bicarbonate as an acid acceptor, the water formed being separated off by distillation during the reaction and the organic phase obtained after the addition of water and separation of the phases being worked up by distillation.

The 2,6-dialkylaniline of the formula II, which according to the invention is to be used in excess, is advantageously employed in amounts of 1.5 to 2.5 mols per mol of alkyl 2-bromopropionate of the formula III. It is also possible to use a smaller or larger excess. However, in general it is not advantageous to use an excess of 2,6-dialkylaniline of the formula II which is less than 1.5 mols per mol of alkyl 2-bromopropionate of the formula III, since the yield and conversion are lower when the excess is as low as this. The use of more than 2.5 mols of 2,6-dialkylaniline of the formula II per mol of alkyl 2-bromopropionate of the formula III has no advantages in respect of the yield and quality of the N-(1'-alkoxycarbonylethyl)-2,6-dialkylaniline of the formula I, and is uneconomical because of the effort associated with the removal of the excess 2,6-dialkylaniline by distillation. Preferably, 1.6 to 1.8 mols of 2,6-dialkylaniline of the formula II are used per mol of alkyl 2-bromopropionate of the formula III.

Suitable quaternary compounds of the formula IV are the chlorides, bromides and iodides and the bisulfates. The quaternary compounds of the formula IV are as a rule used in amounts of 0.5 to 5% by weight, based on the alkyl 2-bromopropionate of the formula III. The use of 1 to 3% by weight of the quaternary compound of the formula IV, based on the alkyl 2-bromopropionate of the formula III, has proved particularly advantageous.

Examples of suitable quaternary compounds of the formula IV are tetrapropylammonium chloride, tetrapropylammonium bromide and tetrapropylammonium iodide, tetrabutylammonium chloride, tetrabutylammonium bromide and tetrabutylammonium iodide, benzyltrimethylammonium chloride, benzyltriethylammonium chloride, benzyltributylammonium chloride, benzyldimethylhexadecylammonium chloride, butyltripropylammonium bromide, tributylmethylammonium chloride, trioctylmethylammonium chloride, phenyltrimethylammonium chloride or phenyltrimethylammonium bromide, phenyltriethylammonium chloride, tricaprylmethylammonium chloride, decyltrimethylammonium chloride, dodecyltrimethylammonium chloride, hexadecyltrimethylammonium chloride, hexadecylpyridinium chloride, dodecylpyridinium bromide, octylpyridinium bromide, tetrabutylphosphonium chloride, tetrabutylphosphonium bromide and tetrabutylphosphonium iodide, benzyltrimethylphosphonium chloride, benzyltributylphosphonium chloride, tributylmethylphosphonium chloride, trioctylmethylphosphonium bromide, hexadecyltributylphosphonium bromide, decyltributylammonium chloride, dodecyltriethylammonium bromide, tetraphenylphosphonium bromide, hexadecyltrimethylphosphonium bromide, tributylmethylphosphonium iodide and tetraphenylphosphonium bromide. Tetrabutylammonium bromide has proved particularly suitable.

According to the invention, suitable acid-binding agents are alkali metal carbonates and alkali metal bicarbonates, such as lithium carbonate, sodium carbonate, potassium carbonate, rubidium carbonate and caesium carbonate, and also lithium bicarbonate, sodium bicarbonate, potassium bicarbonate, rubidium bicarbonate and caesium bicarbonate. Preferred acid-binding agents are sodium carbonate, potassium carbonate, sodium bicarbonate and potassium bicarbonate. As a rule, the acid-binding agents are employed in approximately the stoichiometric amount or in excess. Advantageously, the acid-binding agents are used in an amount of 1-3 equivalents, based on the hydrogen bromide to be bonded. Preferably, 1.1–1.3 equivalents of acid-binding agent are used, based on the hydrogen bromide to be bonded.

Within the indicated temperature range of 110°–125° C., in which the reaction of a 2,6-dialkylaniline of the formula II with an alkyl 2-bromopropionate of the formula III is carried out, temperatures of 115° to 120° C. are preferred. The water formed during the reaction of a 2,6-dialkylaniline of the formula II with an alkyl 2-bromopropionate of the formula III in the presence of an alkali metal carbonate or alkali metal bicarbonate is advantageously separated off during the reaction, by azeotropic distillation.

After the reaction has ended, the reaction mixture is cooled and freed from salts by extraction with water. The excess 2,6-dialkylaniline of the formula II is then separated off from the organic phase by distillation. The removal of the 2,6-dialkylaniline of the formula II by distillation is advantageously effected in vacuo. The N-(1'-alkoxycarbonylethyl)-2,6-dialkylaniline of the formula I, which is obtained as the residue, can as a rule be used in this form for further reactions, for example for the reaction with carboxylic acid chlorides mentioned initially. However, the product can also be purified by vacuum rectification if this is required for a specific application.

According to a preferred embodiment of the process according to the invention, 1.7 mols of 2,6-dialkylaniline of the formula II are employed per mol of alkyl 2-bromopropionate of the formula III and the reaction is carried out at 115° to 120° C. in the presence of 1 to 3% by weight of tetrabutylammonium bromide, based on the amount of alkyl 2-bromopropionate of the formula III employed, and in the presence of 0.55 to 0.65 mol of sodium carbonate per mol of alkyl 2-bromopropionate of the formula III. In particular, 2,6-dimethylaniline and methyl 2-bromopropionate can be reacted advantageously in accordance with this preferred embodiment.

Using the process according to the invention, it is possible to prepare the N-(1'-alkoxycarbonylethyl)-2,6-dialkylanilines of the formula I in higher yields and in better quality than with the processes disclosed hitherto. The process according to the invention can be carried out in a simple manner in conventional equipment and is particularly suitable for continuous operation. In view of the high yield and quality of the process products and the low expenditure on apparatus, the process according to the invention can be regarded as being particularly economical. Compared with known processes, the process according to the invention also offers ecological advantages, since, as a result of the high yield and the high selectivity, only minimal amounts of decomposition products and by-products pass into the effluent.

The process according to the invention is illustrated in more detail by the example which follows.

EXAMPLE

Preparation of N-(1'-methoxycarbonylethyl)-2,6-dimethylaniline 167.0 g (1 mol) of methyl 2-bromopropionate, 206.0 g (1.7 mols) of 2,6-dimethylaniline, 55.0 g (0.52 mol) of sodium carbonate and 5.0 g of tetrabutylammonium bromide are heated to 115°–120° C., with stirring, and kept at this temperature for 6 hours. The water formed during the reaction is distilled off in vacuo. After the reaction has ended, the reaction mixture is cooled to room temperature and stirred with 200 g of water until all of the salts have dissolved. After separating off the aqueous phase, 202 g of an organic phase are obtained; this consists to the extent of about 33% by weight of 2,6-dimethylaniline and to the extent of about 65% by weight of N-(1'-methoxycarbonylethyl)-2,6-dimethylaniline. Separation of the organic phase by distillation yields 190.0 g of N-(1'-methoxycarbonylethyl)-2,6-dimethylaniline and 93.0 g of 2,6-dimethylaniline. The yield of N-(1'-methoxycarbonylethyl)-2,6-dimethylaniline is 98.3%, based on the 2,6-dimethylaniline converted.

What is claimed is:

1. A process for the preparation of N-(1'-alkoxycarbonylethyl)-2,6-dialkylanilines of the formula I

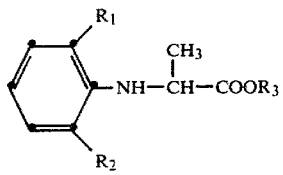

in which $R_1$ and $R_2$ are each methyl or ethyl and $R_3$ is an alkyl group having 1–4 carbon atoms, by reacting a 2,6-dialkylaniline of the formula II

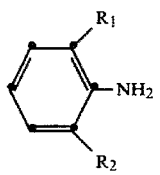

in which $R_1$ and $R_2$ are as defined above, with an alkyl 2-bromopropionate of the formula III

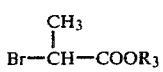

in which $R_3$ is as defined above, which comprises carrying out the reaction of the 2,6-dialkylaniline of the formula II with the alkyl 2-bromopropionate of the formula III at 110°–125° C., in excess 2,6-dialkylaniline as the solvent, in the presence of a quaternary compound of the formula IV

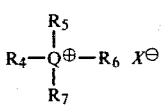

in which Q is nitrogen or phosphorus, the radicals $R_4$, $R_5$, $R_6$ and $R_7$ are each an alkyl radical having 1 to 16 carbon atoms, or phenyl, and one of the radicals $R_4$, $R_5$, $R_6$ and $R_7$ can also be benzyl, and, if Q is nitrogen, Q together with three of the radicals $R_4$, $R_5$, $R_6$ and $R_7$ can also be a pyridine radical, whilst the fourth radical is alkyl having 1–16 carbon atoms, phenyl or benzyl, and $X^\ominus$ is a halide anion or a bisulfate anion, and in the presence of an alkali metal carbonate or alkali metal bicarbonate as an acid acceptor, the water formed being separated off by distillation during the reaction and the organic phase obtained after the addition of water and separation of the phases being worked up by distillation.

2. A process according to claim 1, wherein the 2,6-dialkylaniline of the formula II is employed in an amount of 1.5 to 2.5 mols per mol of alkyl 2-bromopropionate of the formula III.

3. A process according to claim 1, wherein the 2,6-dialkylaniline of the formula II is employed in an amount of 1.6 to 1.8 mols per mol of alkyl 2-bromopropionate of the formula III.

4. A process according to claim 1, wherein the quaternary compound of the formula IV is employed in an amount of 0.5 to 5% by weight, based on the alkyl 2-bromopropionate of the formula III.

5. A process according to claim 1, wherein the quaternary compound of the formula IV is employed in an amount of 1 to 3% by weight, based on the alkyl 2-bromopropionate of the formula III.

6. A process according to claim 1, wherein the quaternary compound of the formula IV which is employed is tetrabutylammonium bromide.

7. A process according to claim 1, wherein the acid-binding agent used is sodium carbonate, potassium carbonate, sodium bicarbonate or potassium bicarbonate.

8. A process according to claim 1, wherein the alkali metal carbonate or alkali metal bicarbonate used as the acid-binding agent is employed in an amount of 1–3 equivalents, based on the hydrogen bromide to be bonded.

9. A process according to claim 1, wherein the alkali metal carbonate or alkali metal bicarbonate to be used as the acid-binding agent is employed in an amount of 1.1–1.3 equivalents, based on the hydrogen bromide to be bonded.

10. A process according to claim 1, wherein the reaction of a 2,6-dialkylaniline of the formula II with an alkyl 2-bromopropionate of the formula III is carried out at a temperature of 115° to 120° C.

11. A process according to claim 1, wherein the water formed during the reaction is separated off by azeotropic distillation.

12. A process according to claim 1, wherein 1.7 mols of 2,6-dialkylaniline of the formula II are employed per mol of alkyl 2-bromopropionate of the formula III and the reaction is carried out at 115° to 120° C. in the presence of 1–3% by weight of tetrabutylammonium bromide, based on the alkyl 2-bromopropionate of the formula III, and in the presence of 0.55 to 0.65 mol of sodium carbonate per mol of alkyl 2-bromopropionate of the formula III.

13. A process according to claim 1, wherein the 2,6-dialkylaniline of the formula II which is used is 2,6-dimethylaniline.

14. A process according to claim 1, wherein the alkyl 2-bromopropionate of the formula III which is used is methyl 2-bromopropionate.

* * * * *